United States Patent [19]

Bott et al.

[11] Patent Number: 5,056,918
[45] Date of Patent: Oct. 15, 1991

[54] METHOD AND APPARATUS FOR PARTICLE SIZE ANALYSIS

[75] Inventors: Steven E. Bott, Conway; Harry R. McKinley, Southampton; W. Howard Hart, Amherst, all of Mass.

[73] Assignee: Coulter Electronics of New England, Inc., Amherst, Mass.

[21] Appl. No.: 319,370

[22] Filed: Mar. 3, 1989

[51] Int. Cl.⁵ .................. G01N 15/02; G01N 21/53
[52] U.S. Cl. .................................. 356/336; 356/343
[58] Field of Search .............................. 356/336, 343

[56] References Cited

U.S. PATENT DOCUMENTS

| | | | |
|---|---|---|---|
| 3,646,352 | 2/1972 | Bol et al. | 290/218 |
| 3,758,787 | 9/1973 | Sigrist | 290/574 |
| 3,809,478 | 5/1974 | Talbot | 356/71 |
| 3,873,206 | 3/1975 | Wilcock | 356/103 |
| 4,017,186 | 4/1977 | Shofner et al. | 356/103 |
| 4,037,965 | 7/1977 | Weiss | 356/102 |
| 4,052,600 | 10/1977 | Wertheimer | 364/554 |
| 4,099,875 | 7/1978 | McMahon et al. | 356/103 |
| 4,134,679 | 1/1979 | Wertheimer | 356/336 |
| 4,167,335 | 9/1979 | Williams | 356/336 |
| 4,274,741 | 6/1981 | Cornillault | 356/336 |
| 4,286,876 | 9/1981 | Hogg et al. | 356/343 |
| 4,341,471 | 7/1982 | Hogg et al. | 356/343 |
| 4,541,719 | 9/1985 | Wyatt | 356/343 |
| 4,595,291 | 6/1986 | Tatsuno | 356/336 |
| 4,648,715 | 3/1987 | Ford, Jr. et al. | 356/344 |
| 4,676,641 | 6/1987 | Bott | 356/336 |
| 4,679,939 | 7/1987 | Curry et al. | 356/336 |

Primary Examiner—Davis L. Willis
Assistant Examiner—Matthew W. Koren
Attorney, Agent, or Firm—Lahive & Cockfield

[57] ABSTRACT

Methods and apparatus for measuring the intensity of light scattered by particles suspended in a sample volume illuminated by an interrogating light beam directed along an input axis, utilizing plural Fourier optical systems having lenses arranged for illuminating multiple photodetectors. The lenses of each Fourier optical system can be of different optical powers, for providing low power and high power optical trains. A low power optical train provides high resolution measurements of light scattered within a small angular range at low angles relative to the input axis, while a high power optical train provides lower resolution measurements of light scattered within a larger angular range at higher angles.

14 Claims, 4 Drawing Sheets

METHOD AND APPARATUS FOR PARTICLE SIZE ANALYSIS

BACKGROUND OF THE INVENTION

This invention relates generally to systems for measuring the size of particles, and, more particularly, relates to apparatus and methods for high resolution measurement of sub-micron and micron particle size distributions using light scattering over a wide rang of scattering angles.

There are several prior art techniques for measuring the size and distribution of sizes of particles in a sample by using light scattering. Generally, to measure the sizes of individual particles, for example, in a flowing stream of a liquid or gas, the particle-containing sample stream is illuminated by a constant light source and the intensity of light scattered by each particle is detected.

A particle scatters the light by an amount related to the particle size. In general, larger particles scatter more light than do smaller particles. The relationship between the amount of scattering and particle size can be determined either from theoretical calculations or through a calibration process. With a knowledge of this relationship, for a single particle at a time, the detected scattered light intensity provides a direct measure of the particle size.

The distribution of particle sizes in a sample can be determined by individually passing each particle in the sample, or a portion of the sample, through the scattered light detection apparatus, and tabulating the sizes of the various particles. In practice, this method is generally restricted to particles larger than 0.5 microns. Moreover, this method is relatively slow, because particles must be presented and detected individually. This technique is referred to in the prior art as optical particle counting.

Another prior art technique of particle sizing by light scattering is referred to as static or "classical" light scattering. This method is based upon illumination of a sample containing the particles to be sized, followed by the measurement of the intensity of scattered light at several predetermined angles. The intensity of light scattered from a particle is a function of the size of the particle, the wavelength of incident light, and the angle at which the scattered light is collected relative to the incident light. This method of particle sizing based upon the angular dependence of the scattered light intensity can be employed to determine the size distribution of a group of particles.

In particular, for particles larger than approximately one micron, scattering in the near-forward direction is well described by Fraunhofer diffraction theory. The Fraunhofer principle yields the angular distribution of scattered light in the focal plane of a lens. For a given particle having a diameter d, the scattered intensity in the angular direction u is given by $$I_{d,u} = k_1 [(\pi d^2)/4]^2 [2J_1(k_2du)/(k_2du)]^2$$

where $k_1$ = a constant;
$k_2$ = $\pi\lambda$; and
$\{J(k_2du)\}$ = a Bessel function The Fraunhofer theory, upon which most conventional laser diffraction systems are based, shows that small particles diffract light at high angles while larger particles diffract light at smaller angles. Accordingly, by analyzing the composite diffraction pattern resulting from the scattering of monochromatic light beam by a given sample, and measuring the intensity of light scattered at predetermined angles, it is possible to deduce the size distribution of particles in the sample. This principle is widely used in laser diffraction methods and apparatus.

The following U.S. patents disclose examples of laser diffraction systems for measurement of particle size:

| | |
|---|---|
| 3,646,652 | Bol et al |
| 3,758,787 | Sigrist |
| 3,809,478 | Talbot |
| 3,873,206 | Willcock |
| 4,017,186 | Shofner et al |
| 4,037,965 | Weiss |
| 4,052,600 | Wertheimer |
| 4,099,875 | McMahon et al |
| 4,167,335 | Williams |
| 4,274,741 | Cornillault |
| 4,286,876 | Hogg et al |
| 4,341,471 | Hogg et al |
| 4,541,719 | Wyatt |
| 4,595,291 | Tatsuno |
| 4,648,715 | Ford, Jr. et al |
| 4,676,641 | Bott |
| 4,679,939 | Curry |

Certain prior art systems, among those disclosed in the above-identified U.S. patents, utilize a single-optical-axis system, which may comprise a single lens or an assembly of lenses disposed along the same optical axis, for collecting forward scattered light—in a range of approximately 0.03–30.00 degrees from the axis of the incident beam—and directing the scattered light into 15–50 discrete detector cells, so that each detector cell is illuminated by light scattered from the particles at a particular scattering angle.

Other prior art systems utilize multiple collection lenses, disposed along different optical axes, the lenses being optically connected to a single photodetector via fiber optic or other optical coupling elements.

The configuration of a typical prior art laser diffraction instrument 110 for particle size analysis is illustrated in FIG. 1. The beam from a laser 112 is expanded by a conventional beam expander assembly 114, in order to cover a large number of particles in a sample and to reduce the divergence of the beam. This parallel beam then passes through the sample 116, typically a dispersion contained in a sample holder 118. The sample 116 can be stirred or pumped through the path of the laser beam in a re-circulation system, if the sample is a suspension or emulsion, or blown or sprayed through if the sample is a dry powder or spray. Light 122 scattered in the near-forward angles is collected by a Fourier transform lens configuration 120 and directed toward a multicell detector 124, arranged such that the position of a given particle in the path of the laser beam does not affect the point at which the light diffracted by that particle falls on the detector 124.

Discrete detector segments or cells on the detector 124 sense the intensity of light corresponding to that scattered at different angles to the incident beam. This intensity profile can be provided to a computer 126 where digital processing elements determine the size distribution of the particles passing through the laser beam. The computer 126 can be controlled by input from a keyboard 128, and can provide data output via a display unit 130 and printer 132.

Diffraction-type particle size measurement instruments are widely used for measuring sample materials having a broad size distribution—i.e., a wide size range—such as dust or pigment particles. Because large particles scatter light at small angles to the axis of an incident beam, and smaller particles scatter light at large angles, particle size measuring systems utilizing scattered light detection must be capable of measuring scattered light intensity over a large range of scattering angles. Additionally, because large particles scatter light at small angles, and relatively large changes in their size produce only small changes in scattering angles, it would be advantageous to measure light scattered at small angles with relatively high resolution.

These two requirements pose conflicting demands on a single Fourier transform lens system, such as lens system 20 shown in FIG. 1. The result, in conventional diffraction instruments, is compromised performance at large angles, small angles, or both.

A limited range of measurement angles—approximately 20-60 degrees—can be achieved in a conventional diffraction system for measurement of particle size, using a single lens and multiple detectors in a Fourier lens system. Alternatively, a wide range of measurement angles, with sparse coverage within the angular measurement range, can be attained with multiple detectors, each coupled with a single lens or system of apertures to define the scattering angle, or by moving a single detector successively to different scattering angles. Each of these approaches has been implemented in certain prior art devices, and each has significant limitations.

In particular, when a single-axis optical system is utilized for collecting scattered light over a wide angular range, a short focal length system can provide detection at large angles, at the cost of compressing low-angle scattered light near the optical axis, where it may be obscured by laser spill-over or rendered unresolvable by the finite size of detector segments.

When attempts are made to overcome these deficiencies by utilizing lenses of longer focal length, further problems arise, especially in measurement of scattered light at higher angles. In particular, the longitudinal displacement of high angle detectors from the optical axis can require large dimensions, resulting in a cumbersome instrument package. The required displacement (R) of detectors from the optical axis is approximately $$R = [FL] \tan[theta]$$

where [FL] = focal length of the lens [theta] = scattering angle in the sample cell.

In addition, such a system would require large diameter lenses for collecting light scattered at large angles, thereby increasing spherical aberration and astigmatism and complicating the positioning of high angle detectors.

Systems which utilize elements for moving a single detector successively to different scattering angles are typically limited by low angular resolution, long measurement times and mechanical complexity.

Accordingly, it is an object of the invention to provide methods and apparatus for analysis of particle size based upon measurement of scattered light, which enable the measurement of scattered light over wide angular ranges.

It is another object of the invention to provide methods and apparatus for measuring particle size with high angular resolution at low scattering angles.

It is a further object of the invention to provide particle size analysis apparatus which is compact and mechanically reliable.

Other general and specific objects of the invention will in part be obvious and will in part appear hereinafter.

SUMMARY OF THE INVENTION

The foregoing objects are attained by the invention, which provides methods and apparatus including a multiple-axis optical system, for measuring the intensity of light scattered by particles suspended in a sample volume illuminated by an interrogating light beam directed along an input axis. The system includes plural Fourier lens systems, each arranged on a different optical axis, each collecting scattered light for illuminating multiple photodetectors.

In one aspect of the invention, the multiple lenses of the Fourier lens systems are of different optical powers, for providing low power and high power optical trains. The low power optical train provides high resolution intensity measurement of light scattered within a small angular range, at low angles to the input axis. The high power optical train provides intensity measurement of light scattered within a larger angular range, at larger angles to the input axis.

The plural optical trains can be configured for measuring scattered light over different respective angular segments relative to the axis of the beam. In accordance with another aspect of the invention, the plural optical trains are arranged for measuring scattered light over a common angular range. This aspect of the invention can include elements for combining the intensity data detected by each optical train into a single profile of relative intensity correlated with angular position. This aspect of the invention can also include elements for generating an error signal when intensity values measured at common angles by the plural optical trains fail to agree.

Another aspect of the invention includes a photodetector array for measuring the intensity of scattered light, including a monolithic silicon structure having a plurality of discrete annular silicon photodetector sectors disposed about a surface-mounted mirror positioned on the nominal beam axis. The innermost sectors measure light scattered at small angles, and the outermost sectors measure light scattered a larger angles.

Annular sectors corresponding to the lowest scattering angles are small, to provide maximum resolution at low scattering angles. Annular sectors corresponding to progressively larger scattering angles are progressively larger in radial and circumferential dimension, so that sector area generally increases exponentially with scattering angle.

Moreover, sectors nearest the mirror are disposed quasi-symmetrically about the mirror, for measuring small overlapping angular ranges of scattered light. Sectors farther from the mirror are disposed symmetrically about the mirror, for measuring congruent ranges of scattered light. A single row or "tail" of equal-sized sectors can extend from the outermost one of the increasing sized sectors. The tail sectors measure light scattered at angles greater than a selected angle. A second monolithic detector array can be disposed adjacent the first, for measuring light scattered at angles beyond that measured by the outermost tail sector.

The invention will next be described in connection with certain illustrated embodiments. However, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENTS

Figure 1:
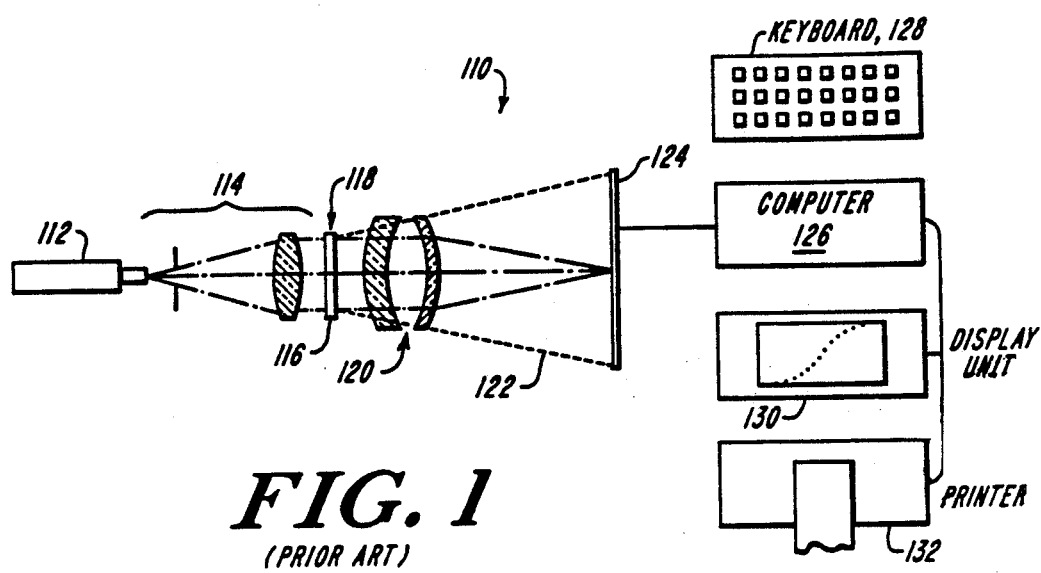
FIG. 1 is a schematic diagram illustrating a conventional laser diffraction apparatus for particle size analysis.
Figure 2A:
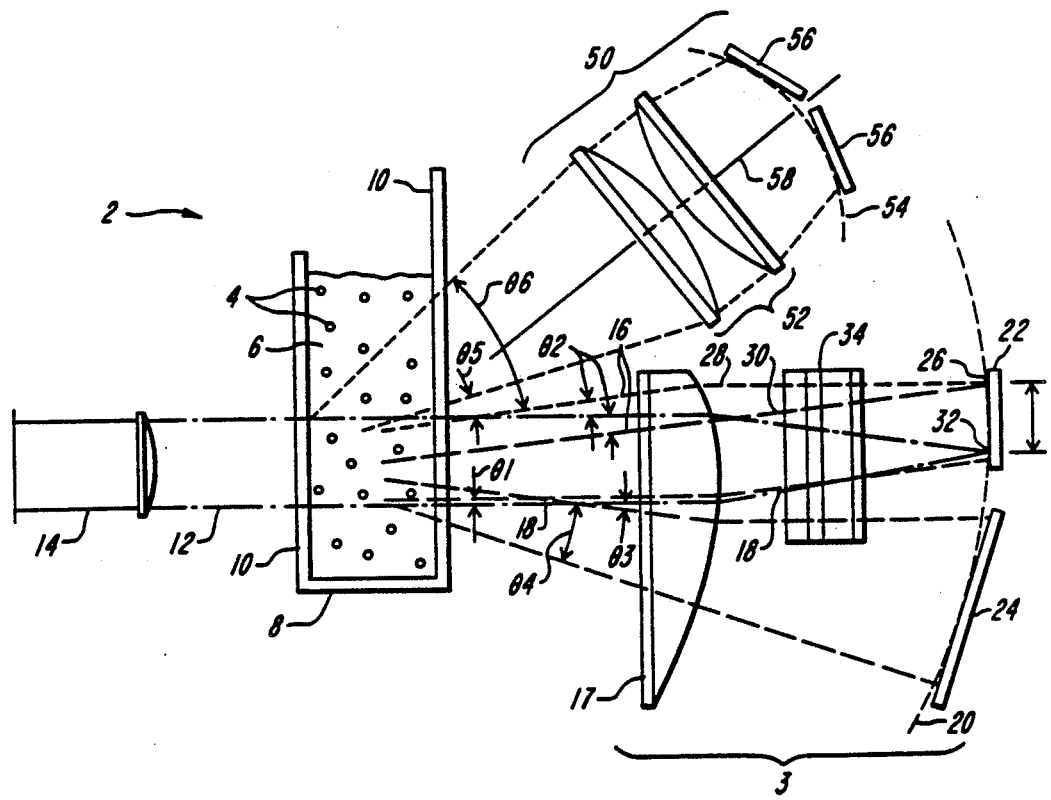
FIG. 2A depicts particle size analysis apparatus according to the invention.
Figure 2B:
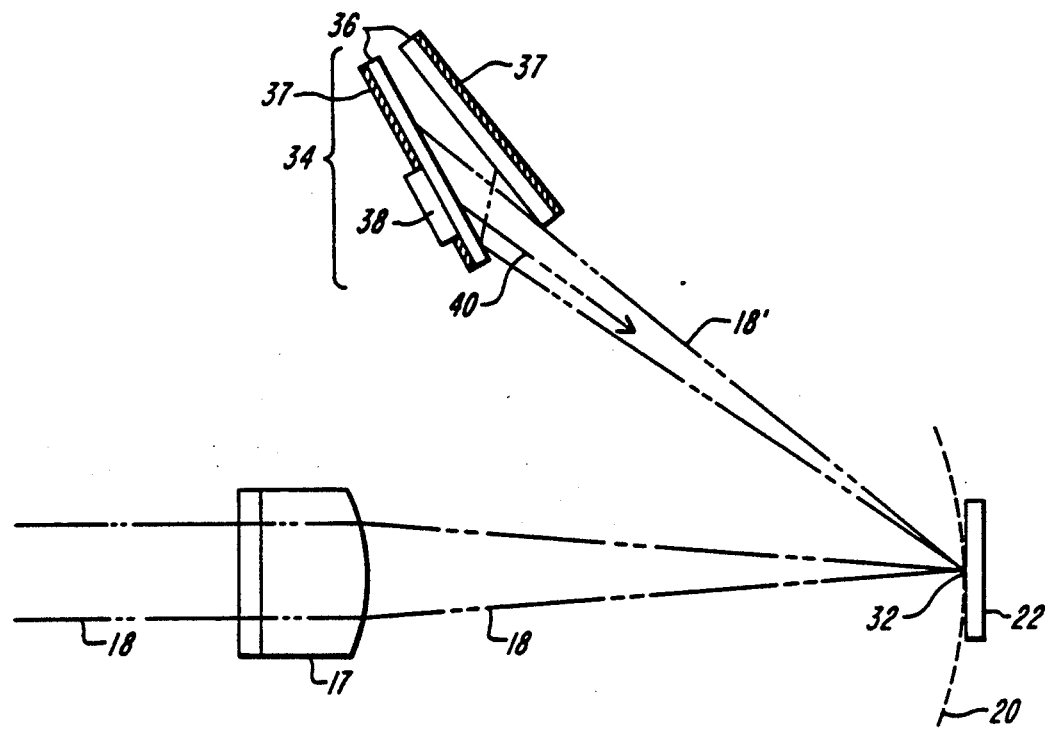
FIG. 2B depicts a light trap for use with the apparatus of FIG. 2A.

FIGS. 2A and 2B depict a particle size analysis system 2 constructed in accordance with the invention, for measuring the size distribution of particles 4 suspended in a fluid 6 and contained in a sample cell 8. In accordance with conventional engineering practice, the walls 10 of sample cell 8 can be constructed of a transparent material, such as glass or plastic, for admitting an interrogating beam 12 of light. Beam 12 can be a substantially parallel beam of monochromatic light, generated by a conventional light source including a laser, spatial filter, and collimator 14 of known design and construction. The beam 12 is transmitted through the walls 10 of sample cell 8, where particles 4 to be analyzed scatter a portion of the light 16 at various angles to the axis of the beam 12. As discussed above, the amplitude and angle of the scattered light is in part a function of particle size.

The term "scattering angle", as defined herein, denotes the angle between the direction of propagation of the interrogating beam and the direction of propagation of light scattered from the sample volume. In particular, a given portion of the scattered light will diverge from the direction of propagation of the interrogating beam by an angle theta.

The unscattered portion 18 of the beam 12 passes out of the sample cell 8 and into a set of optical components collectively referred to herein as lower optical train 3. The unscattered beam 18 is transmitted through a lower collecting lens 17 which focuses the beam 18 to a point on a mirror element 32 on the focal surface 20 defined by a photodetector array 22. Lens 17 can be a conventional lens for use in a Fourier lens system constructed in accordance with known engineering practice.

Focal surface 20 can be inclined toward the sample cell 8, so as to be substantially tangent to the circumferential dashed line indicated in FIG. 2A. The focal surface 20 has associated therewith photodetector arrays 22 and 24, described in greater detail hereinafter in connection with FIGS. 3, 4A, 4B, 5A and 5B. In accordance with the invention, focal surface 20 is positioned so that the distance between the lens 17 and the focal surface 20 is equal to the focal length of the lens 17.

A portion of the light 16 scattered by particles 4 in the sample cell 8 also passes through the lens 17 and toward the focal surface 20. Those skilled in the art will appreciate that when focal surface 20 is positioned so that the distance between the lens 17 and the focal surface 20 is equal to the focal length of the lens 17, light scattered at angle $\theta_2$ the input axis of the beam 12, at any location in the sample cell 8, will fall on approximately the same point 26 at the focal surface 20. This is illustrated in FIG. 2A by exemplary light rays 28 and 30.

As a result, each location on focal surface 20 receives light scattered at a single, unique angle to the input axis of the beam 12 in the sample cell 8. By measuring light intensity at small discrete locations at the focal surface 20, the intensity/angle profile of light scattered by particles 4 in the sample cell 8 can be determined. Conventional light scattering theory, such as Fraunhofer or Mie scattering, can then be applied to determine the approximate particle size distribution in the sample cell 8, based upon this intensity/angle profile.

If the focal surface 20 is displaced forward or backward, the angle-mapping relationship between lens 17 and surface 20 no longer applies. Rays scattered at the same angle, such as rays 28 and 30, no longer fall on exactly the same point on surface 20, and a single detector point 26 will collect a mixture of light from different angles, thereby providing a less precise measurement estimate of particle size distribution.

Referring again to FIG. 2A, light scattered at higher angles in the sample cell 8 passes into a second set of optical elements, referred to herein as the upper optical train, denoted collectively by reference numeral 50 in FIG. 2A. The included light, illustrated by exemplary rays $\theta 5$ and $\theta 6$, is transmitted through a collection lens 52 to a second detection surface 54. This detection surface 54 is related to its collection lens 52 in the same manner that surface 20, in the lower optical train, is related to its respective collection lens 17. Specifically, the detection surface 54 is displaced from the collection lens 52 by a distance equal to the focal length of the lens 52. Preferably, the detection surface 54 is substantially spherical, rather than flat.

In the embodiment illustrated in FIG. 2A, the lowest angle of scattered light $\theta 5$ entering the upper optical train can be slightly smaller than the angle corresponding to $\theta 4$, and the highest angle of scattered light $\theta 6$ entering the optical train can be several times greater. Thus, the optical train 50 collects high angle light scatter over a wider angle than does the lower Optical train. Moreover, because the smallest angle $\theta 5$ is less than the largest angle $\theta 4$ measured by the lower optical train 3, both optical trains measure a certain portion of light which is scattered at the same angles relative to the input axis defined by beam 12. A first portion of scattered light is defined herein to have the "same" or "comparable" scattering angle as a second portion, when the first portion diverges from the interrogating beam by an angle of the same magnitude as that of the second portion, and falls in the plane defined by the axis of the interrogating beam and the second portion. The overlapping angular ranges of the upper and lower optical trains permit the illustrated apparatus to measure a continuous, uninterrupted intensity/angle profile in the angular range between $\theta 1$ to $\theta 6$.

The focal length of collection lens 52 can be, for example, 118 millimeters, while that of collection lens 17 can be 2.5 times greater, or 293 millimeters. As a result, the detection surface 54 is 2.5 times closer to its respective lens than is surface 20, and the light scatter from $\theta 5$ to $\theta 6$ is compressed along the detection surface 54 by a factor of 2.5 compared with that along the surface 20. These values are provided solely by way of example, and other optical values can be utilized in accordance with the invention.

The invention has been described in connection with a "binocular" optical configuration utilizing two optical pathways for collecting scattered light and directing this light onto detector arrays. Those skilled in the art will recognize that the invention can be advantageously practiced in connection with apparatus utilizing a greater number of optical pathways, providing the advantages of measurement over a large angle and high resolution at small angles.

Figure 3:
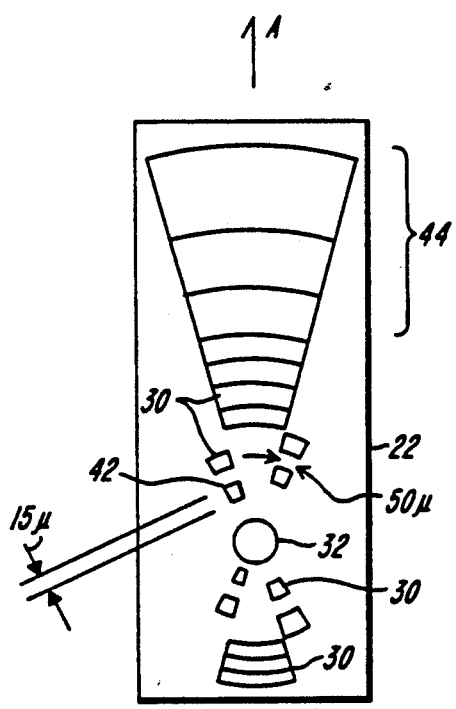
FIG. 3 is a schematic diagram depicting an embodiment of a photodetector array utilized in connection with the apparatus of FIG. 2A.

Moreover, the invention can be practiced in conjunction with a variety of photodetector array configurations, including certain conventional photodetectors. In accordance with a preferred practice of the invention, however, a low angle photodetector such as that depicted in FIG. 3 is utilized. The surface 20 has associated therewith a central mirror element 32 and two silicon detector arrays 22 and 24. The inner detector 22 is a monolithic silicon structure which can include sixty-two discrete silicon sectors 30 are substantially annular in form. As illustrated in FIG. 3, these sectors are disposed so as to radiate outward from central mirror 32, which defines the position upon which the light source is focused.

The innermost sector 42 measures light scattered at small angles to the beam 12, while the outer sectors 44 measure light scattered at greater angles. The innermost sector 42 can be located slightly outside the point of spillover from the light beam. This spillover is an effect well known in the art, and results from small imperfections in the optical elements. In a preferred practice of the invention, sector 42 is constructed as small as manufacturing practices permit, to achieve optimum resolution. Thus, the radial width of the sector 42 can be, for example, approximately 15 microns, while the arc length of sector 42 can be approximately 50 microns. In the illustrated embodiment, the detector sectors increase progressively in radial width and arc length, providing an exponential increase in the areas of the sectors.

Preferably, sectors proximate the mirror 32 can be quasi-symmetrically disposed, to measure small, overlapping angular ranges of scattered light. Farther from mirror 32, the sectors can be symmetrically arranged, for measuring comparable angles of scattered light. Additionally, a single row of sectors 44, referred to as a "tail," measures light scattered at progressively higher angles. In the embodiment illustrated in FIG. 2A, for example, the axis A—A (FIG. 3) of detector 22 can be oriented vertically with the "tail" sectors 44 extending upwards.

Moreover, in the embodiment illustrated in FIG. 2A, a second detector array 24 can be located on a vertical axis below detector 22. This array 24 measures light scattered at higher angles to the incident beam 12 than does detector 22. In particular, detector 22 measures scattered between $\theta 1$ and $\theta 2$ while detector 24 measures between $\theta 3$ and $\theta 4$.

Figure 4A:
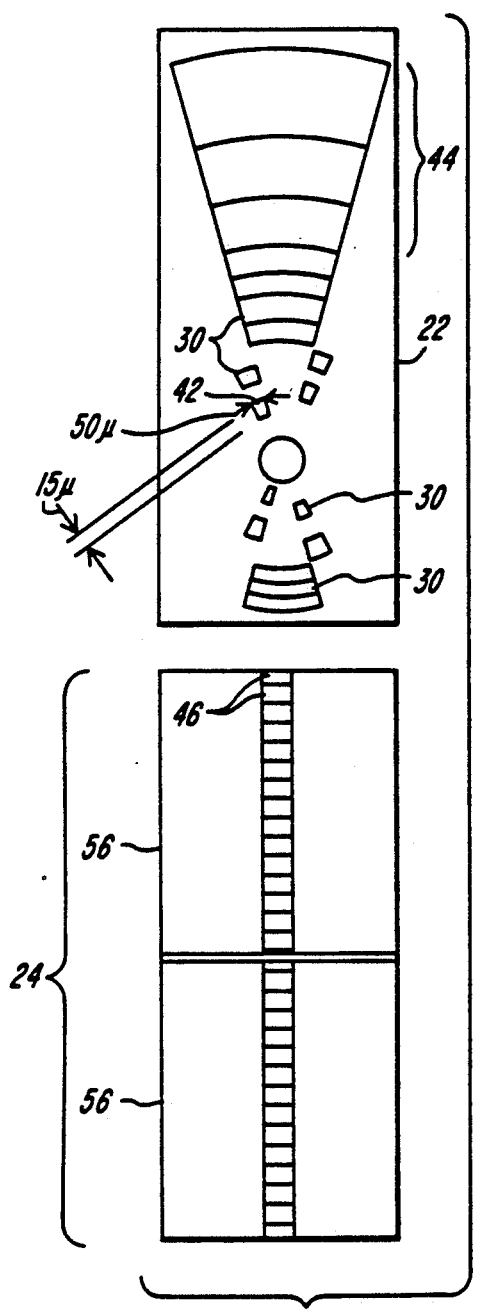
FIGS. 4A and 4B depict front and side views, respectively another embodiment of photo detectors which can be employed in the apparatus of FIG. 2A.
Figure 4B:
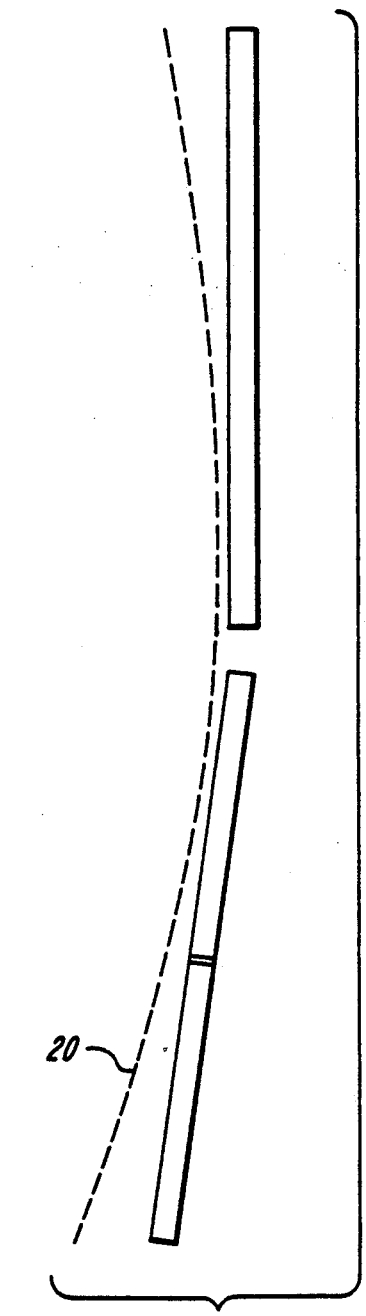

This orientation is further illustrated in FIGS. 4A and 4B, which provides a front and side views, respectively of detector arrays 22 and 24. FIGS. 4A and 4B also indicates that detector array 24 is an assembly of two monolithic, linear silicon arrays. Detector array 24 can, for example, include sixteen sectors, each 1.58 millimeters long and 1.22 millimeters wide. The arrays from which detector assembly 24 is constructed can include conventional detector elements manufactured by United Detector Technology, marketed as Part No. A2V-16.

In one embodiment of the invention, as indicated in FIG. 4A, detector array 22 is asymmetrical, having tail sectors 44 extending outward on one side of central mirror 32. This configuration allows the inner sectors 46 of detector 24 to be positioned proximate to the optical center of mirror 32, and allows the innermost sectors 46 of detector array 24 to measure light scattered at angles near $\theta 3$ which are comparable to those angles—i.e. $\theta 2$—measured by the outermost tail sectors 44 of detector 22. The optical overlap of sectors 44 and 46 permits the particle size analysis system to measure a continuous, uninterrupted intensity profile from $\theta 2$ to $\theta 4$.

In accordance with this detector design, the employment of first sectors which increase exponentially in area, and other sectors which increase linearly or are of constant area, reduces the dynamic range required of associated signal amplifiers and signal conversion electronics utilized for processing sector signals. These signals typically have a wide dynamic range, and have heretofore posed significant difficulties in the design of signal processing electronics.

In particular, at small angles, where light scattered from large particles is of interest, observed light intensity falls off rapidly with angle. In this region, exponentially increasing sectors tend to yield signals of the same order of magnitude, thus simplifying subsequent electronic processing. At high angles, observed light intensity falls off in a substantially more linear manner. Accordingly, in this region, sectors which increase linearly in area, or which have constant area, tend to yield signals of the same order of magnitude, likewise reducing dynamic range requirements.

Additionally, at higher scattering angles, linear detectors have been observed to provide greater resolution. The resulting improved spectral detail associated with smaller particles is advantageous in quantifying anomalies associated with complex Mie light scattering effects, which occur when a particle size approaches the wavelength of interrogating light.

Detector geometry in accordance with the invention thus enables increased dynamic range of measurement and increased resolution, while reducing the dynamic range required of associated signal processing electronics.

In a further preferred embodiment of the invention, as illustrated in FIG. 4B, the detector arrays 22 and 24 are inclined inwardly, toward the collection lens 17, in order to maintain the forward surface of the detector sectors close to the surface 20. The surface 20 is preferably a substantially spherical surface corresponding to the surface of best focus of the collection lens 17. Positioning the active face of the sectors of the detectors on or near this surface 20 maximizes focus, and minimizes the mixing of light scattered at different angles at each sector's surface, thereby enhancing measurement precision.

Figure 5A:
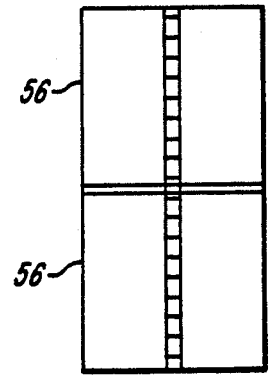
FIGS. 5A and 5B depict a further example of photodetectors utilized in connection with the apparatus of FIG. 2A.
Figure 5B:
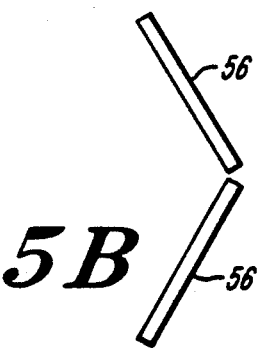

The upper optical train detector arrays 56, corresponding to detection surface 54, are depicted in FIGS. 5A and 5B. In particular, FIG. 5B indicates that the detector arrays 56 are inclined toward the optical axis 58 of collection lens 52, in order to better conform to the spherical nature of the detection surface 54. Detector arrays 56 can include two United Detector Technology, Part No. A2V-16 silicon arrays as described above in connection with FIG. 4. These detector arrays 56 measure scattered light between $\theta 5$ and $\theta 6$ indicated in FIG 2A.

Figure 6:
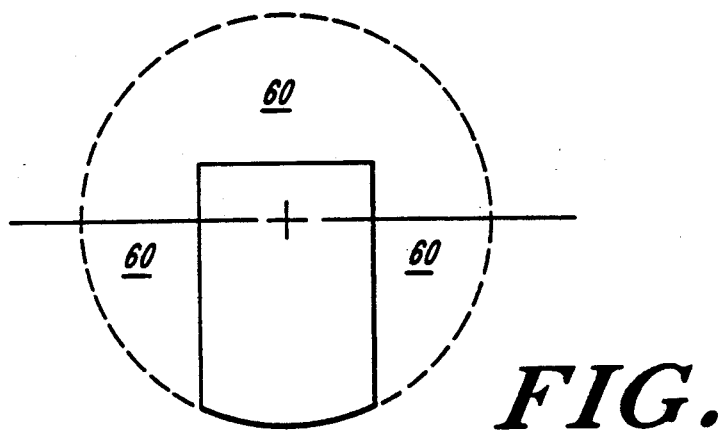
FIG. 6 is a schematic diagram illustrating a lens configuration employed in accordance with the invention.

The particle size analysis system of the invention can utilize a variety of lens designs for collecting scattered light. The high angle collection lens 52, as illustrated in FIG. 2A, can be a doublet, a configuration which provides a lens with a large aperture and short focal length. One configuration of the low angle lens 17 is a substantially spherical lens, having three sides 60, and truncated as illustrated in FIGS. 2A and 6. In order to minimize beam spillover, the interrogating beam is directed through the optical center of the lens. The sides of the lens perform no function, and thus can be removed. In addition, the upper portion of the lens 17 can be removed to facilitate positioning of the upper collection lens 52 so that both lenses 17 and 52 can collect light at comparable scattering angles from a given illuminated sample volume.

Referring again to FIG. 2A, those skilled in the art will recognize that the upper lens 52 can be further displaced upward, and that lens 52 can be positioned to collect light at angles as small as $\theta 4$. Displacement of lens 52 to this extent would preclude measurement over a comparable angular segment, but would provide a continuous measurement of the intensity profile to $\theta 6$. This configuration offers the advantages of further reduced spatial requirements and a physically smaller instrument package.

Figure 7:
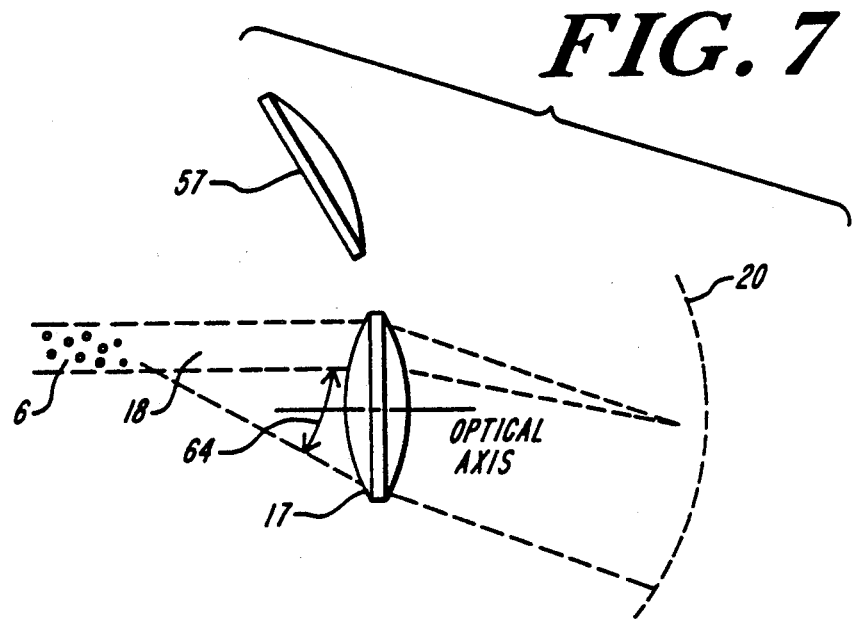
FIG. 7 depicts a practice of the invention utilizing a selected optical axis offset.

Alternatively, cutting of lens 17 can be avoided by directing the interrogating light beam 18 to pass, not through the optical center of the lower lens 17, but through a region of lens 17 offset from the optical center, as depicted in FIG. 7. This displacement permits upper lens 52 to be positioned for collecting light flux down to $\theta 4$, so that a continuous measurement of intensity is obtained. In this alternative embodiment, however, the focus of the beam 18 becomes non-optimal, and laser spillover will be increased, thus reducing low angle sensitivity.

In a preferred embodiment of the invention, as indicated in FIG. 2A, collection lens 17 can be a "landscape" or plano-convex lens oriented with its planar face facing the sample cell 8. Lenses of the plano-convex type ordinarily collect a substantially parallel bundle of light from each distant element in a landscape, and direct each such bundle onto a single position on a light-sensitive medium, such as a CCD array or the film of a camera. In the particle size analysis system of the invention, the light of interest is composed of rays scattered from the sample cell 8 at substantially the same angle, forming a bundle of parallel light. Because the precision of a diffraction instrument is improved by focusing all light scattered at a given angle to a single point, the plano-convex lens is advantageously utilized in the invention.

This employment of the plano-convex lens is contrary to conventional engineering practice. In conventional imaging devices, such as photographic apparatus, the distance from the object to the lens is much greater than the distance between the lens and the image, and sharp images are produced by orienting the planar surface of the lens toward the image. If a plano-convex lens were utilized in this conventional orientation in a diffraction instrument—i.e., with the planar surface facing the detector—the angular "blur" due to aberrations would be unacceptable. Designers of conventional diffraction instruments have therefore concluded that plano-convex lenses are of limited utility in such instruments, and have instead utilized expensive achromat lenses to obtain sufficiently sharp angular resolution.

We have found, however, that by positioning a suitable plano-convex lens in an orientation opposite that of the conventional orientation, angular resolution substantially equal to that attainable with an achromat can be achieved, with a less expensive plano-convex lens. This unexpected result arises because the plano-convex lens is applied herein for a different purpose—i.e., in a Fourier lens system in a diffraction instrument, rather than to form an image, as employed conventionally.

In accordance with the invention, therefore, the plano-convex lens can be oriented with its planar surface facing the sample volume, and spaced sufficiently far from the sample volume so that spherical aberration and astigmatism are minimized. The configuration illustrated in FIG. 2A offers a combination of lens 17 and sample cell 8 offering minimum field curvature and astigmatism, and thus maximum resolution.

One deficiency of certain conventional laser diffraction apparatus used for analysis of particle size is a reduction in resolution due to interference by extraneous light. Thus, a preferred embodiment of the invention utilizes a light trap or "beam dump" module. Referring to FIGS. 2A and 2B, the interrogating light beam 18 can be directed onto mirror 32 and reflected into a light trap 34. As shown in FIG. 2B, the light trap 34 can be composed of two converging pieces of dark material 36, such as glass, and preferably, a photodetector 38 for monitoring the power of the reflected beam 18'. The converging angle of the glass 36 can be approximately 9 degrees, an angle which causes the beam 18' to make approximately seven reflections before re-emerging toward the surface 20. Because the glass is optically coated, each reflection reduces the intensity of the re-emerging beam 40 by a factor of approximately $10^2$. Seven reflections therefore yield a $10^{14}$ reduction in the power of the emerging beam 40. Accordingly, the emerging beam 40 has an immeasurably small effect as it returns toward the surface 20.

The optically coated dark glass 36 can be, for example, three millimeter thick NG1 glass manufactured by Schott Glass Technologies Inc. This material attenuates transmitted light by a factor of approximately $10^6$. In the light trap 34, where light passing into the glass 36 must pass through it, strike a wall 37, and then re-emerge through the glass 36, the power of emerging light is therefore reduced by a factor in excess of $10^{12}$.

The detector 38 can be, for example, a commercial silicon detector with a sensitive surface of about 0.4×0.8 inches in dimension. Such a detector is manufactured by EG & G Vactec Division. The detector 38 can be positioned on one side of a dark glass element 37.

The invention thus provides a number of advantages over conventional particle size measurement methods and apparatus. As discussed above, certain conventional devices utilize a single optical train to provide measurements over a wide angle of scattered light. In these devices, a short focal length system permits detection to greater angles, but compresses low angle scatter near the optical axis, where it may be obscured by laser spillover or rendered unresolvable by the finite size of a detection segment. Other conventional devices attempt to address this problem by employing a longer focal length lens, at the expense of increased spatial requirements, greater spherical aberration and astigmatism, and increased complication in positioning high angle detectors.

The multiple optical pathways of the invention offer the advantages of compactness and enhanced optical resolution. In addition, multiple lens trains, even of the same focal length, offer economic advantages. While the low angle lens train must be of high quality to minimize scatter and spillover—which reduces low angle resolution—the high angle lens train need not meet this requirement. This is because the interrogating light beam does not pass through the high angle lens train. This lens can be manufactured to less stringent tolerances, and thus may be less expensive.

Moreover, lens fabricating costs are approximately proportional to lens area, or the square of lens diameter. Replacing a single, large-diameter lens with two lenses of approximately half the diameter can reduce lens cost by approximately 50%.

In addition to these general advantages, the utilization of optical trains having different focal lengths permits a wide measurement span at high angles, and high resolution at low angles. Different power optical trains permit the use of a common detector design for both high and low resolution measurements, and allow greater flexibility in the selection of detector arrays. The designer can select a low angle array with sector areas which grow exponentially to compensate for the rapid decay of intensity at high angles, and high angle arrays with sector areas that are constant or increase linearly to compensate to the slow decay of intensity in this region.

It will thus be seen that the invention efficiently attains the objects set forth above, among those made apparent from the preceding description.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that following claims are intended to cover all of the generic and specific features of the invention as described herein, and all statements of the scope of the invention which, as a matter of language, might be said to fall therebetween.

Having described the invention, what is claimed as new and secured by Letters Patent is:

1. In a system for measuring the size of particles suspended in a sample volume, including illumination means for illuminating the sample with a light beam directed along an input axis, and plural photodetectors for measuring the intensity of light scattered by the sample, the improvement comprising
   first light collector means, including at least a first Fourier lens system including a first lens for collecting light scattered over small angles relative to the input axis and illuminating a first set of the plural photodetectors therewith, said first lens and said first set of detectors of said first Fourier lens system being positioned so that said first set of detectors are substantially in the Fourier locus determined with respect to said sample volume and
   second light collector means, including at least a second Fourier lens system including a second lens, for collecting light scattered over greater angles relative to the input axis and illuminating a second set of the plural photodetectors therewith, said second lens and said second set of photodetectors of said second Fourier lens system being positioned so that said second set of photodetectors are substantially in the Fourier locus determined with respect to said sample volume.

2. In a system according to claim 1, the further improvement wherein
   said first Fourier lens system is characterized by a first optical power, and
   said second Fourier lens system is characterized by a second optical power greater than said first optical power.

3. In a system according to claim 2, the further improvement wherein said first light collector means and said second light collector means collectively and simultaneously collect light scattered over a comparable angular segment relative to the input axis.

4. In a system according to claim 1, the further improvement comprising
   first photodetector means, including a first set of discrete photodetector sectors having selected areas, for detecting light scattered over small angles relative to the input axis, each sector of said first set being arranged for detecting light scattered over an angular range about a corresponding measurement angle, wherein the respective areas of successive sectors of said first set increases exponentially as a function of increasing measurement angle, and
   second photodetector means, including a second set of discrete photodetector sectors, for detecting light scattered over greater angles relative to the input axis, each sector of said second set being arranged for detecting light scattered over an angular range about a corresponding measurement angle, wherein the respective areas of successive sectors of said second set increases linearly as a function of increasing measurement angle.

5. In a system according to claim 4, the further improvement wherein
   first sectors of said first set are disposed in proximity to, and quasi-symmetrically about, the reference axis, for measuring overlapping angular ranges of scattered light, and
   second sectors of said first set are disposed symmetrically about the mirror, for measuring congruent ranges of scattered light.

6. In a system according to claim 5, the further improvement comprising third photodetector means, including a set of equal-sized sectors extending from the outermost one of the increasing sized sectors, for detecting light scattered at angles greater than a selected angle.

7. In a system according to claim 1, the further improvement wherein
said first light collector means includes selector means for collecting light having a first wavelength, and
said second light collector means includes selector means for collecting light having a second wavelength.

8. In a system according to claim 1, the further improvement wherein at least one of said lenses in said Fourier lens systems is a substantially plano-convex lens having a substantially planar surface oriented toward the sample volume, said substantially plano-convex lens being spaced sufficiently far from the sample volume so that any of spherical aberration and astimagtism are minimized.

9. A method for measuring the size of particle suspended in a sample volume, the method comprising the steps of
illuminating the sample with a light beam directed along an input axis,
configuring a plurality of photodetectors to measure the intensity of light scattered by the sample,
configuring at least a first Fourier leans system including a first lens to collect light scattered over small angles relative to the input axis to illuminate a first set of said photodetectors therewith, said first lens and said first set of detectors of said first Fourier lens system being positioned so that said first set of detectors are substantially in the Fourier locus determined with respect to said sample volume,
said step of configuring at least a first Fourier lens system includes the step of configuring said first lens to have first optical power, and
configuring at least a second Fourier lens system including a second lens to collect light scattered over greater angles relative to the input axis to illuminate a second set of said photodetectors therewith, said second lens and said second set of photodetectors being positioned so that said second set of photodetectors are substantially in the Fourier locus determined with respect to said sample volume
said step of configuring at least a second Fourier lens system includes the step of configuring said second lens to have a second optical power greater than said first optical power.

10. A method according to claim 9 wherein said step of configuring at least a first Fourier lens system includes the step of configuring said first lens to have first optical power, and
said step of configuring at least a second Fourier lens system includes the step of configuring said second lens to have a second optical power greater than said first optical power.

11. A method according to claim 10 comprising the further step of positioning said first Fourier lens and said second Fourier lens to collectively and simultaneously collect light scattered over a comparable angular segment relative to the input axis.

12. A method according to claim 9 wherein said step of configuring a plurality of photodetectors includes the steps of
configuring a first set of discrete photodetector sectors having selected areas to detect light scattered over small angles relative to the input axis, said configuring of said first set including
arranging each sector of said first set to detect light scattered over an angular range about a corresponding measurement angle, and
selecting respective areas of successive sectors of said first set to increase exponentially as a function of increasing measurement angle, and
configuring a second set of discrete photodetector sectors to detect light scattered over greater angles relative to the input axis, said configuring of said second set including
arranging each sector of said second set for detecting light scattered over an angular range about a corresponding measurement angle, and
selecting respective areas of successive sectors of said second set to increase linearly as a function of increasing measurement angle.

13. A method according to claim 12 comprising the further steps of
positioning first sectors of said first set in proximity to, and quasi-symmetrically about, the reference axis, to measure overlapping angular ranges of scattered light, and
positioning second sectors of said first set symmetrically about the mirror, to measure congruent ranges of scattered light.

14. A method according to claim 13 comprising the further step of positioning a set of equal-sized photodetector sectors to extend from the outermost angle covered by the increasing sized sectors, to detect light scattered at angles greater than said outermost angle.

* * * * *